United States Patent [19]

Sabel et al.

[11] Patent Number: 5,114,719
[45] Date of Patent: May 19, 1992

[54] EXTENDED DRUG DELIVERY OF SMALL, WATER-SOLUBLE MOLECULES

[76] Inventors: Bernhard A. Sabel, Kreuzberg 6, 8011 Egmating, Fed. Rep. of Germany; Andrew Freese, 115 Whitcomb Ave., Jamaica Plain, Mass. 02130

[21] Appl. No.: 407,418

[22] Filed: Sep. 14, 1989

Related U.S. Application Data

[63] Continuation-in-part of Ser. No. 43,695, Apr. 29, 1987, Pat. No. 4,883,666.

[51] Int. Cl.$^5$ .............................................. A61F 13/00
[52] U.S. Cl. ................................... 424/422; 424/486; 424/487; 424/473; 424/426; 424/422
[58] Field of Search ................ 424/486, 487, 473, 426, 424/422

[56] References Cited

U.S. PATENT DOCUMENTS

| | | | |
|---|---|---|---|
| 153,896 | 8/1874 | Le Pivert | 431/303 |
| 3,263,273 | 8/1966 | Appelgren et al. | 425/451.7 |
| 3,518,150 | 6/1970 | Theurer | 156/426 |
| 3,625,214 | 12/1971 | Higuchi | 424/424 |
| 3,851,648 | 12/1974 | Brooke | 424/473 X |
| 3,887,699 | 6/1975 | Yolles | 424/473 X |
| 3,948,254 | 4/1976 | Zaffaroni | 128/833 |
| 3,965,255 | 6/1976 | Block et al. | 424/450 |
| 3,976,071 | 8/1976 | Sadek | 424/425 |
| 4,008,719 | 2/1977 | Theeuwes et al. | 424/473 X |
| 4,016,880 | 4/1977 | Theeuwes et al. | 424/473 |
| 4,034,758 | 7/1977 | Theeuwes et al. | 424/473 X |
| 4,278,087 | 7/1981 | Theeuwes | 424/405 |
| 4,351,337 | 9/1982 | Sidman | 424/425 |
| 4,391,797 | 7/1983 | Folkman et al. | 424/425 |
| 4,432,802 | 2/1984 | Harata et al. | 424/473 X |
| 4,475,916 | 10/1984 | Himmelstein | 424/473 X |
| 4,675,189 | 6/1987 | Kent et al. | 424/490 |

FOREIGN PATENT DOCUMENTS

| | | |
|---|---|---|
| 0168862 | 1/1986 | European Pat. Off. |
| 0226061 | 6/1987 | European Pat. Off. |
| 2167662 | 6/1986 | United Kingdom |

OTHER PUBLICATIONS

A. D. Schwope, et al. *Chemical Abstracts* 84, 304 Abstract No. 84:184849x.
R. Willette, *Chemical Abstracts* 84(13) 304 Abstract No. 184855w (Jun. 28, 1976).
Suzuki and Price *Journal of Pharmaceutical Sciences* 74(1) 21-24 (Jan. 1985).
Cardinal, "Matrix Systems", Chapter 2, *Medical Applications of Controlled Release*, vol. 1, 41-67, 87-89 (CRC Press, Inc., Florida 1984).

(List continued on next page.)

*Primary Examiner*—Thurman K. Page
*Assistant Examiner*—William E. Benston, Jr.
*Attorney, Agent, or Firm*—Kilpatrick & Cody

[57] ABSTRACT

A polymeric device releasing biologically active, water-soluble materials having a molecular weight of less than 1000 in a controlled, continuous and linear manner over an extended period of time. Insoluble polymer matrixes can be defined in any shape, size and drug content. When applied to medical use, biocompatible polymers are used so that the device is implantable. The device is made by modifying prior art devices based on diffusion of fluid into a polymeric matrix containing dispersed biologically active molecules to yield a polymer device which can be placed in a fluid environment, so that fluid is absorbed by the device and the water soluble molecules diffuse into the fluid environment, leaving behind pores and channels, where the rate of diffusion is limited by an impermeable coating over a portion of the polymeric matrix and/or by adjusting the drug loading to produce the number and size of pores and channels to the surface of the polymeric matrix yielding the desired release rate of the biologically active molecules. The device is characterized by several distinguishing features: a mechanism usually associated with macromolecular release which is applicable to small, water soluble molecules and controlled, long term linear release of large drug quantities.

5 Claims, 4 Drawing Sheets

OTHER PUBLICATIONS

Siegel, R. A., et al., *Pharm. Res.* 1, 2-10 (1984).
Rhine, et al., *J. Pharm. Sci.* 69(3), 265-270 (1980) *.
Sladek, et al. *J. Neurosurg.* 68,377-351 (1981).
Cotzias, et al, *New Eng. J. Med.* 276(7) 374-379 (Feb. 16, 1967).
Yahr, et al, *Arch. Neurol.* 21, 343-354 (Oct. 1969).
Rossor, et al, *J. Neurolog. Sci.* 46, 385-392 (1980).
Juncos, et al, *Neurol.* 37, 1242-1245 (Jul. 1987).
Juncos, et al, *J. Neurol. Neurosurg. Psych.* 50, 194-198 (1987).
Quinn, et al, *Lancet* 412-415 (Aug. 21, 1982).
Shoulson, *Neurol.* 25, 1144-1148 (Dec. 1975).
Mouradian, et al, *Ann. Neurol.* 22, 475-479 (1987).
Martin, *JAMA* 216(12), 1979-1983 (Jun. 21, 1971).
Tolosa, et al., *Neurol.* 25, 177-183 (Feb. 1975).
Nutt, *Ann. Neurol.* 22, 535-540 (Mar. 3, 1987).
Mars, *Arch. Neurol.* 28,91 (Feb. 1973).
Juncos, et al, *Arch Neurol.* 44, 1010-1012 (Oct. 1987).
Bergmann, et al, *Adv. Neurol. 45, 463-467n (1986).*
Brady, *Molecular Basis of Lysosomal Storage Disorders* 461-474 (Academic Press 1984).
Pincus, et al, *Arch. Neurol.* 44, 1006-1009 (1987).
Saarinen, et al, *Acta Neurol. Scandinav.* 58, 340-349 (1978).
Birket-Smith, et al, *Lancet* 431-432 (Feb. 24, 1973).
Cedarbaum, et al, *Neurol.* 37, 233-241, 1607-1612 (1987).
Curzon, et al, *Lancet* 781 (Apr. 7, 1973).
Woods, et al, *Lancet* 1391 (Jun. 16, 1973).
Chase, et al, *Adv. in Neurol.* 45, 477-480 (1986).

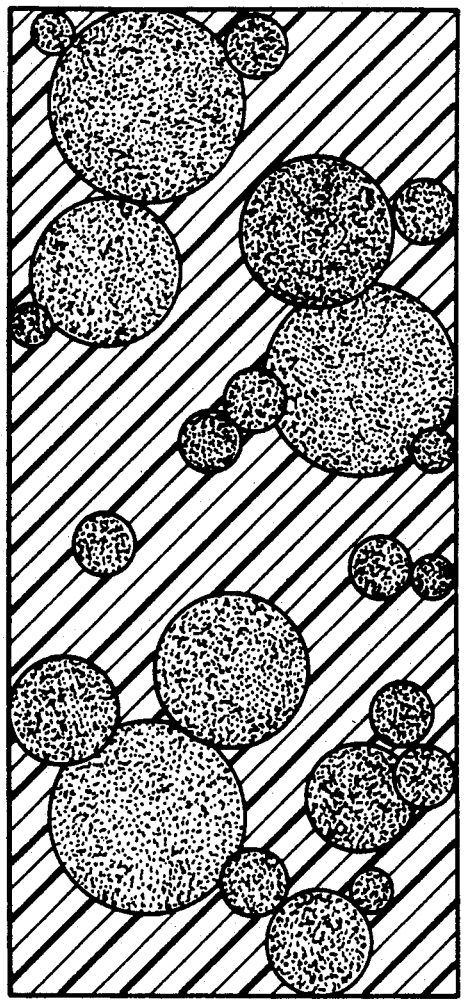
fig. 6
fig. 7
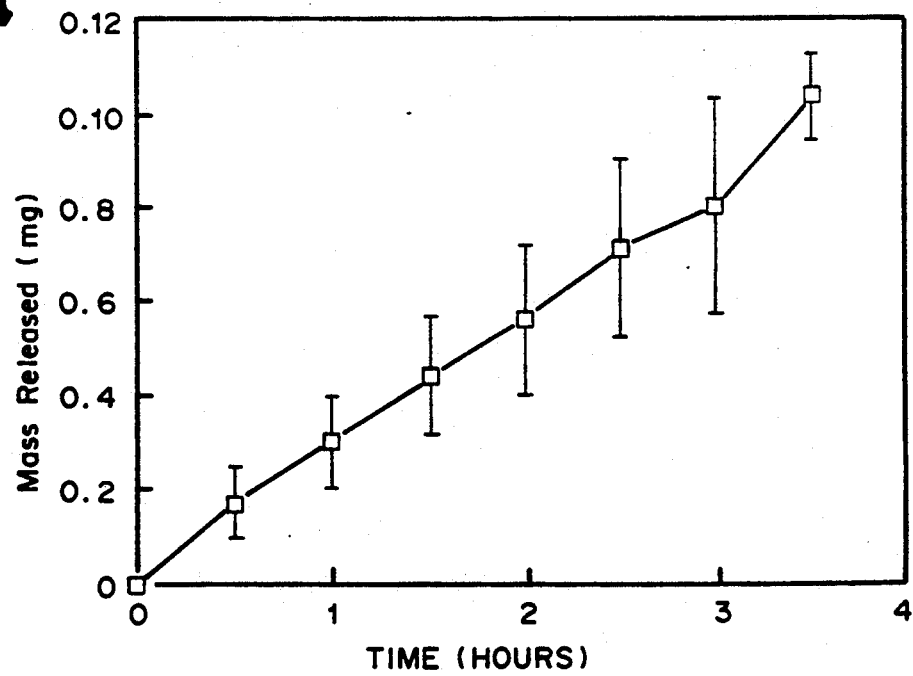

EXTENDED DRUG DELIVERY OF SMALL, WATER-SOLUBLE MOLECULES

The U.S. Government has rights in this invention by virtue of this research supported in part by N.I.H. Grant GM26698.

This is a continuation-in-part application of U.S. Ser. No. 07/043,695 "Controlled Drug Delivery System for Treatment of Neural Disorders", filed Apr. 29, 1987, by Bernhard A. Sabel, Andrew Freese, and Mark Saltzman, issued Nov. 28, 1989, as U.S. Pat. No. 4,883,666.

BACKGROUND OF THE INVENTION

This invention is generally in the field of drug delivery devices for the controlled release of small, water-soluble molecules. Particularly, the disclosed system is a polymeric composition useful for the controlled and continuous delivery of biologically active drugs from a non-erodible, hydrophobic polymer matrix device.

In recent years great efforts have been made to develop polymeric compositions which are capable of delivering active agents, particularly drugs, over extended periods of time in a controlled fashion. The purpose of these systems is to deliver such drugs at a predictable and predetermined rate to achieve a desired physiological or pharmacological effect. For example, see U.S. Pat. No. 4,391,797 to Folkman, et al.; U.S. Pat. No. 4,069,307, to Higuchi, et al.; and U.S. Pat. No. 3,948,254, to Zaffaroni.

A number of polymeric devices have been developed to control the release of low molecular weight (less than 1000) drugs. See, for example, A. C. Tanquary and R. E. Lacey, eds., *Controlled Release of Biologically Active Agents,* (Plenum, New York). In almost all cases, the mechanism of release is the diffusion of the drug through a solid polymer, and diffusion rates are generally low, as discussed by Siegel and Langer, *Pharmaceutical Research,* 1, 2-10 (1984). While the devices disclosed by the prior art possesses desirable release kinetics for a variety of low molecular weight substances with low or no water solubility, these devices are limited in that they do not release drugs with high water solubility for extended periods of time in a controlled, zero-order fashion. "Zero-order" is defined as a linear relationship between amount released and time of release.

The difficulty of obtaining zero-order release of water-soluble molecules for long time periods is apparent when one considers the release mechanism of drugs from polymeric matrix devices. Polymeric devices function by passive diffusion of the molecules either through the polymer itself, for low molecular weight molecules, or through a matrix of channels and pores, for macromolecules. Diffusion is not only dependent on factors such as drug loading, matrix coating or drug particle size, but is also greatly influenced by the water solubility and molecular weight of the drug embedded in the matrix, discussed by Rhine, et al., *J. Pharmaceutical Sciences,* 69(3), 265-270 (1980). Thus, molecules which are either very large, defined as molecules having molecular weights greater than 1000, or poorly water-soluble, will be retained in the matrix more readily and zero-order release kinetics will be more easily achieved. It is similarly apparent that drugs with good water solubility will diffuse readily and polymeric devices containing such drugs release the embedded drug relatively quickly, in a non-linear fashion, not with zero-order release kinetics for long time periods. Another factor which plays a major role is the nature of the polymer itself, i.e., biodegradable versus non-biodegradable, and the degradation kinetics.

As the following table shows, the prior art discloses sustained and/or controlled release of small molecules from polymeric devices, but the drugs being released were water insoluble or almost insoluble and of low molecular weight. The approximate molecular weight (m.w.) and solubility in water is taken from "The Merck Index, 10th Edition", (Merck & Co., Rahway, N.J., 1983).

TABLE 1

Molecular weight and solubility of compounds released from prior art polymeric devices.

| Drug | M.W. | Solubility | Reference |
|---|---|---|---|
| Progesterone | 314 | Insoluble | Higuchi U.S. Pat. No. 4,069,307 Zaffaroni U.S. Pat. No. 3,948,254 Dick UK Pat. 2,167,662A |
| Diethylstilbestrol | 268 | almost insoluble | Higuchi U.S. Pat. No. 4,069,307 |
| Estradiol | 272 | almost insoluble | Zaffaroni U.S. Pat. No. 3,948,254 Dick UK Pat. 2,167,662A |
| Medroxyprogesterone | 341 | insoluble | Higuchi U.S. Pat. No. 4,069,307 |
| Digoxin | 781 | almost insoluble | Appelgren U.S. Pat. No. 4,263,273 |
| Nandrolone | 274 | insoluble | Dick UK Pat. 2,167,662A |

In summary, the prior art discloses sustained or controlled-release of drugs of low molecular weight from polymeric devices, but such drugs were primarily molecules which were either insoluble or almost insoluble in water.

Another factor known to influence release kinetics of polymeric compositions is the molecular weight of the drug embedded into the matrix. The prior art discloses various devices to release macromolecules for an extended period of time. For example, W. D. Rhine et al., *J. Pharmaceutical Science,* 69(3), (1980) report a fabrication method that allows for the controlled release of serum albumin (M. W. of 68,000). It is noted, however, that linear release was only obtained when the drug loading of the polymeric device was below 37.5%. Also, U.S. Pat. No. 4,164,560 to Folkman discloses release of proteins from a polymeric device, where linear (zero-order) release was observed from day 40 to day 100, at which time the device was empty. Similarly, U.S. Pat. No. 4,675,189 to Kent, et al., reports release of a water soluble polypeptide (LH-RH, m.w. 1182.33), but release is merely sustained, not linear.

If one considers the length of time with which controlled drug delivery was obtained it becomes obvious that the length of time precludes the use of the various devices for a number of clinical applications. For example, if it is desired to treat chronic neurological disorders which affect the nervous system, such as Parkinson's disease, then long-term controlled linear release of clinically useful amounts of a therapeutic agent, such as L-DOPA, would be desirable. Such a device has not been available. The following table indicates the time of linearity, the total linear period as well as the references of the prior art devices.

TABLE 2

Linearity of release of compounds from prior art polymeric devices.

| Time of linearity | total linear period | First Author/Inventor | reference |
|---|---|---|---|
| hr. 6–12 | 6 hrs. | Appelgren | U.S. Pat. No. 4,263,273 |
| hr. 1–4 | 3 hrs. | Bloch | U.S. Pat. No. 3,965,255 |
| Days 56–105 | 51 days | Dick | UK Pat 2,167,662 |
| Days 22–105 | 83 days | Folkman | U.S. Pat. No. 4,391,797 |
| day 40–140 | 100 days | Sidman | U.S. Pat. No. 4,351,337 |
| hrs. 20–70 | 50 hrs. | Theeuwes | U.S. Pat. No. 4,278,087 |
| hrs. 4–11 | 7 hrs. | Theeuwes | U.S. Pat. No. 4,217,898 |
| days 14–39 | 25 days | Yolles | U.S. Pat. No. 3,880,991 |
| not provided | not provided | Higuchi | U.S. Pat. No. 3,832,252 |
| hrs. 36–180 | 6 days | Michaels | U.S. Pat. No. 4,177,256 |
| hrs. 40–180 | 5.8 days | Suzuki & Price | J.Pharm.Sci. 74(1)(1985) |

While these polymeric devices are useful for dispensing a number of agents, there may be instances where it would be desirable to provide a degree of control of release for small and water-soluble molecules which is greater than that provided by the prior art. For example, fluid, rapid, short-term release may not be desirable in situations involving release of an agent which is very water soluble. The prior art does not disclose a composition or method whereby water-soluble molecules that have a m.w. of less than 1000 can be released at a controlled, zero-order rate for any appreciable period of time.

U.S. Pat. No. 4,883,666 describes several examples in which dopamine and L-Dopa are released from ethylene vinyl acetate polymeric devices. In one example in U.S. Pat. No. 4,883,666, dopamine, a substance readily soluble in water, is very rapidly released at a non-linear rate when no coating surrounds the loaded polymer core. Linearity was only obtained when a nonpenetrable barrier was formed around the polymer core and a hole in the coating permitted the solution to have access to the loaded core of the device. The need to form a barrier around a loaded core greatly limits the use of such devices, largely because the absolute amount of drug that can be released from such a device is relatively small, generally insufficient for clinical use.

It is therefore an object of the present invention to provide a delivery device allowing long-term, linear release of small, less than 1000 m.w., water-soluble molecules, and method for use thereof.

Another object of the present invention is to provide a small polymeric device that can release a relatively large amount of low molecular weight, water soluble drug.

SUMMARY OF THE INVENTION

A polymeric device releasing biologically active, water-soluble materials having a molecular weight of less than 1000 in a controlled, continuous and linear manner over an extended period of time. Insoluble polymer matrixes can be defined in any shape, size and drug content. When applied to medical use, biocompatible polymers are used so that the device is implantable. The device is made by modifying prior art devices based on diffusion of fluid into a polymeric matrix containing dispersed biologically active molecules to yield a polymeric device which can be placed in a fluid environment, so that fluid is absorbed by the device and the water soluble molecules diffuse into the fluid environment, leaving behind pores and channels, where the rate of diffusion is limited by an impermeable coating over a portion of the polymeric matrix and/or by adjusting the drug loading to produce the number and size of pores and channels to the surface of the polymeric matrix yielding the desired release rate of the biologically active molecules. The device is characterized by several distinguishing features: a mechanism usually associated with macromolecular release which is applicable to small, water soluble molecules and controlled, long term linear release of small, water-soluble molecules in large quantities.

BRIEF DESCRIPTION OF THE DRAWINGS

FIG. 1 is a cross-sectional view through polymers containing L-DOPA; visualization of the structure by scanning electron-microscopy (300×).

FIG. 6 is a schematic cross-section of the dopamine/copolymer devices of FIG. 5 showing the solid particles (dark) of dopamine encapsulated in a continuous polymer phase. Although the polymer phase, which is small (500 to 700 μm for dopamine loaded polymers and 2 mm for L-DOPA loaded polymers) is impermeable to the encapsulated molecules, release occurs as water enters the pore space, dissolving the solid particles. Molecules counter diffuse out of the polymer through the pore network created by dissolution.

FIG. 7 is the short term time course of cumulative release of dopamine from dopamine/ethylene vinyl acetate copolymer matrices. Each experimental point is the mean (± standard deviation) cumulative mass of dopamine released for 4 sample matrices containing 40% loading with a fully coated matrix except for a single cavity. Quadruplicates of matrices containing 0% loading released no dopamine.

DETAILED DESCRIPTION OF THE INVENTION

Figure 1A:
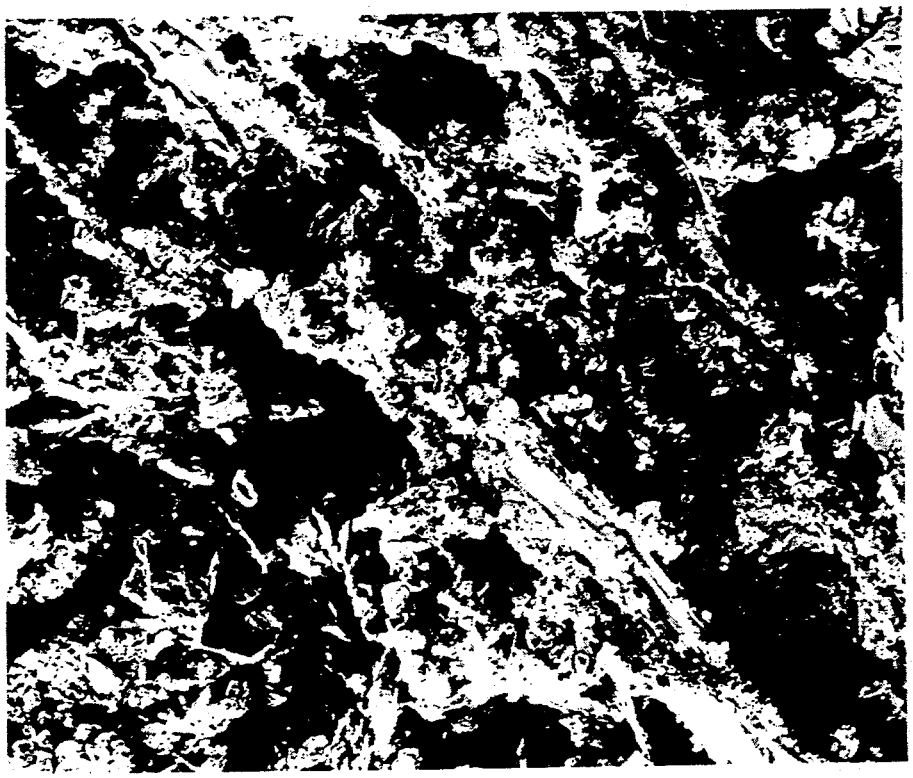
FIG. 1A is a polymer which was fabricated under pore-forming conditions according to the prior art, Rhine, et al., *Controlled Release of Bioactive Materials* pp. 177–187 (Academic Press, New York 1980).

Polymers such as ethylene vinyl acetate copolymer are manufactured into a continuous drug delivery system for small molecules which are water-soluble. "Water-soluble" as used herein is defined as soluble in water to a degree which is greater than "almost insoluble", as defined in the Merck Index ("The Merck Index, 10th Edition", Merck & Co., Rahway, N.J., 1983). The device is a matrix-system. The term "matrix" as used herein is defined as a polymeric carrier matrix that is biocompatible and sufficiently resistant to chemical and/or physical destruction by the environment of use such that the matrix remains essentially intact throughout the release period. The polymer matrices should be biocompatible, plastically deformable, have limited water sorptivity, and be to a limited extent permeable to the passage of small, aqueous-soluble molecules. The term "aqueous" as used herein includes biological fluids, saline and physiological buffer solutions.

Polymeric materials suitable for forming the matrix include the naturally occurring and commercially available polymers, such as acyl substituted cellulose acetates and alkyl derivatives thereof; partially and completely hydrolyzed alkylene-vinyl acetate copolymers, unplasticized polyvinyl chloride, crosslinked homo- and copolymers of polyvinyl acetate, crosslinked polyesters of acrylic and methacrylate; polyvinyl alkyl ethers; polyvinyl fluoride, silicone; polycarbonate, polyurethane; polyamide, polysulphones; styrene acrylonitrile copolymers, crosslinked poly(ethylene oxide); poly(alkylenes); poly(vinyl imidazole); poly(esters); poly(ethylene terephthalate); and chlorosulphonated polyolefines.

In the preferred embodiment, the polymeric material useful for forming the matrix is the ethylene-vinyl acetate copolymer (EVA) commercially available from Dupont (Elvax 40W). Techniques for preparation of these copolymers are disclosed in U.S. Pat. Nos. 2,200,429; 2,398,785; and 2,947,735, in British Pat. Nos. 589,927 and 582,093, and in *Crystalline Olefin Polymers,* edited by Raff, R. A. V., and Doak, V. W., Part II, pp. 261 to 266, (Interscience Publishers Inc., New York 1964).

The present invention will be further understood with reference to the following non-limiting examples demonstrating controlled, long term release of L-DOPA. The devices were prepared by a modification of the method of preparation described by Rhine et al., "Polymers for sustained macromolecule release: procedure to fabricate reproducible delivery systems and control release kinetics", *J. Pharmaceutical Sciences,* 69(3), 265-270 (1980), and U.S. Pat. No. 4,391,797 to Folkman and Langer). L-DOPA was used as a test substance since it has a m.w. of 197.19 and a water solubility of 66 mg/40 ml ("The Merck Index, 10th Edition", Merck & Co., Rahway, N.J., 1983).

The delivery device is a two-phase system which is manufactured using standard techniques such as blending, mixing or the equivalent thereof, following selection of the biologically active material to be delivered and an appropriate polymer for formation of the matrix. The general method which was modified to fabricate the device of the present invention is that of solvent casting as disclosed by Siegel and Langer, "Controlled release of polypeptides and other macromolecules", *Pharmaceutical Research* 1, 2-10 (1984). Briefly, the drug, for example, L-DOPA, is mixed with the polymer, EVA, in a solvent, methylene chloride, the mixture is charged into a frozen mold, and freeze-dried under vacuum.

Using this method as described by the prior art resulted in polymer samples with undesirable release kinetics. However, scanning electron microscopic visualization of the polymer section loaded with L-DOPA revealed that polymers fabricated with the prior art methods displayed pores and channels even before the matrix had released any drug. It was therefore apparent that fluid could gain access to all layers of the polymeric device in a short period of time, with resulting rapid and nonlinear diffusion of the drug into the environment.

In order to obtain preferred release kinetics, the prior art method was altered to prevent channel and pore formation, thus reducing the accessibility of the fluids to the loaded core of the polymer and extending the period in which release of the drug takes place. The alterations of the fabrication method considered desirable included the following steps: 1. reduction of relative solvent quantity used for mixing the drug with the polymer (EVA), 2. substantially eliminating freeze-drying, and 3. application of vacuum during the entire evaporation phase. The amount of solvent was reduced since rapidly evaporating solvent might contribute to pore-information. This was a particular concern when the polymer was then dried by freezing (−20° C.). As a result, the polymer crystallization induced by freezing was only limited to the step where the glass mold was charged with liquid matrix containing dispersed drug particles and lasted for only a few minutes or hours. Alternatively, the evaporation phase was performed at a room temperature in order to reduce pore formation in the core of the polymer. Pore formation occurs more readily when the slab remains at −20° C. for several days, as is standard in the prior art. It is also advantageous to conduct the evaporation step under vacuum at room temperature to provide further significant reductions in pore formation.

Figure 1B:
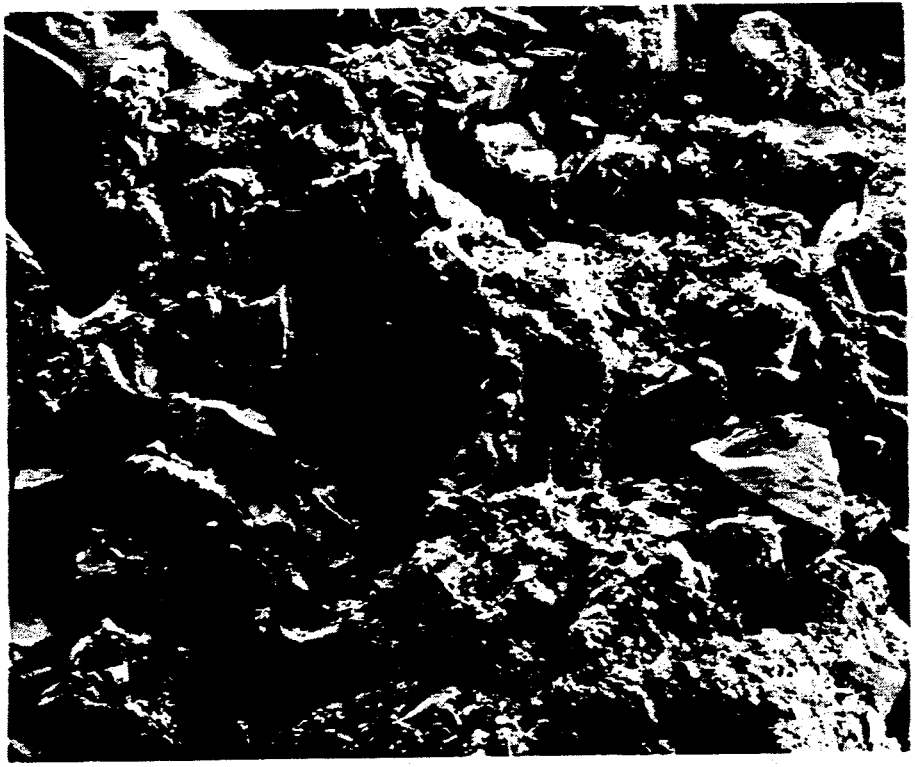
FIG. 1B is a polymer which was made according to the modified fabrication procedure of the present invention.

The result of these modifications are polymer matrixes that contain very few channels and pores, as shown in FIG. 1B, samples of which were subsequently evaluated for release kinetics of L-DOPA. The prior art polymeric devices are shown in FIG. 1A.

Based on this fabrication technology, a two-phase system can be manufactured for delivering a physiologically effective amount of a small (less than 1000 m.w.) and water-soluble pharmacologically active molecule.

Such a device can be implanted in animals and humans to produce a localized or systemic effect.

The composition formed by the method described above consists of a two-phase system having an interpenetrating phase of an agglomerate of a plurality of clusters of small, water-soluble molecules that form at higher loading of the polymer a network of substantially contiguous particles in the polymeric matrix phase.

EXAMPLE OF IN VITRO RELEASE OF L-DOPA FROM EVA.

Ethylene vinyl acetate copolymer (EVA) washed and slabs containing 50%, 55%, 60%, 65%, 70%, 75% or 80% (w/w) L-DOPA (Sigma, St. Louis, Mo.) were prepared according to the following procedure: The polymer was first dissolved in a minimum amount of methylene chloride solvent at 37° C. for 24 hrs. An L-DOPA suspension was thoroughly mixed with the liquified polymer and cast in a frozen rectangular glass mold at −60° C., followed by evaporation as described above. Vacuum was applied until the sample solidified. Rectangular samples were then cut out of the raw slabs.

For control purposes, quadruplicate samples of either loaded polymer matrix surrounded completely by a non-permeable barrier or an unloaded (blank) polymer without L-DOPA was prepared. In order to gain insight into the release kinetics of L-DOPA loaded polymers and to identify polymers with preferred release kinetics, the non-permeable coat was initially applied to reduce diffusion, thereby extending the time window of linear release. The following samples were prepared in quadruplicates: (a) a non-coated polymer to obtain maximum release quantity, (b) a coated polymer where all sides were sealed except for one face of the slab, to combine high release quantity with linearity, or (c) polymers which were fully coated with the exception of a pore through which the medium could gain access to the loaded core. In the non-coated polymers, however, the quantity of release was expected to be maximum.

The solidified polymer was coated with an impermeable polymer barrier in such a way that various polymer geometries were obtained for purposes of comparisons of release characteristics. In order to coat the matrices with an impermeable layer of EVAc, the matrix was first impaled on a 30 gauge needle. The matrix was immersed in liquid nitrogen for 10 to 15 seconds and then immersed in a 20% (w/v) solution of EVAc in methylene chloride. The coated matrix was held under house vacuum for several hours and the procedure was repeated. When the needle was removed from the twice coated matrix, a pinhole cavity remained in the otherwise impermeable coating. By measuring the size of the resulting polymeric device, the thickness of this impermeable coating was calculated to be approximately 500-700 μm. For coating one side of the matrix, the procedure was identical except that the matrix was not fully immersed in the polymer solution. Fully coated polymer matrices were produced by i) pouring a thin film of 10% (w/v) EVAc/methylene chloride into a level mold on dry ice, ii) waiting 10 to 15 minutes for this bottom layer to freeze completely, iii) placing EVAc/dopamine matrices on top of this pure EVAc layer, and iv) carefully pouring a second film of 10% EVAc/methylene chloride into the dry ice temperature mold. The mass of eVAc in each layer was adjusted to obtain a 500-700 μm thick coating on each face of the matrix. This sandwich matrix was evaporated for two days at −20° C. and two days are room temperature under house vacuum. Fully coated devices were obtained by cutting around the encapsulated matrix.

Quadruplicates of these devices were then separately incubated in vials containing a 150 mM NaCl, 0.2% EDTA (as antioxidant) solution, and maintained on an Orbitron oscillating platform (Boekel Industries, Pa.) in a 37° C. oven. In vitro release was monitored by spectrophotometric analysis at 280 nm of the bathing solution, which was replaced each time a measurement was taken. Quantification of dopamine levels was based on comparison to a standard solution curve. The identity of the compound released at various time points was confirmed as greater than 99.9% dopamine by use of High Performance Liquid Chromatography (HPLC) analysis using an Allex 100A pump; a 20 μl sample Rheodyne loop; a 3 μm HR-80 column (ESA, Bedford, Mass.); and an ESA 5100A coulometric detector with an inline conditioning cell. The mobile phase consisted of sodium phosphate, 0.6 g/L; heptane sulfonic acid, 350 mg/L; EDTA, 80 mg/L; and methanol, 5% v/v; pH 4.2. The flow rate was 1.8 ml/mn. Chromatograms for dopamine, dihydroxyphenylacetic acid (DOPAC) and homovanillic acid (HVA) were completed within 12 minutes.

EVALUATION OF L-DOPA RELEASE FROM POLYMER

Quadruplicates of the L-DOPA containing polymer devices were individually immersed in glass scintillation vials containing 20 ml of 150 mM NaCl, 0.2% EDTA solution (as antioxidant) and then incubated at 37° C. on a light protected oscillating platform. L-DOPA release was determined in bi-weekly intervals by spectrophotometric analysis (OD 280), replacing the bathing solution each time measurements were taken to avoid saturation of the solution. The release rate was calculated by comparison to spectrophotometric evaluation of known standards and the authenticity of L-DOPA was confirmed at various time points using high performance liquid chromatography (HPLC). The polymer itself or possible breakdown products resulted in no appreciable absorption at 280 nm.

RESULTS

Figure 2:
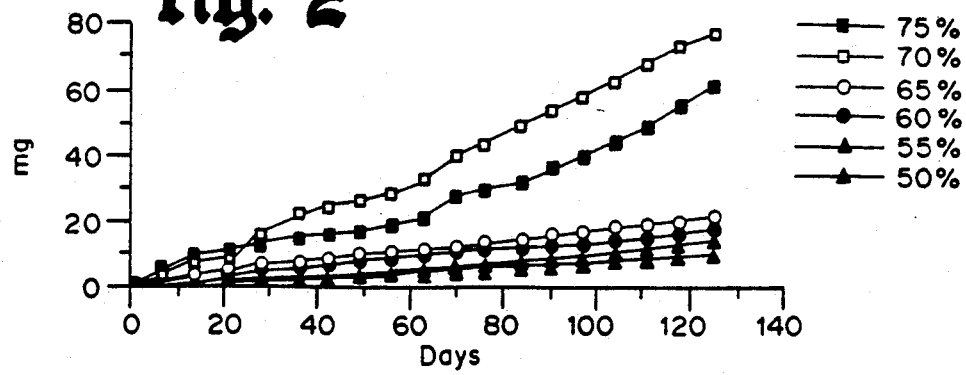
FIG. 2 is a graph showing the cumulative L-DOPA release from polymers which were surrounded by a non-permeable coat containing a 2 mm hole.
Figure 3:
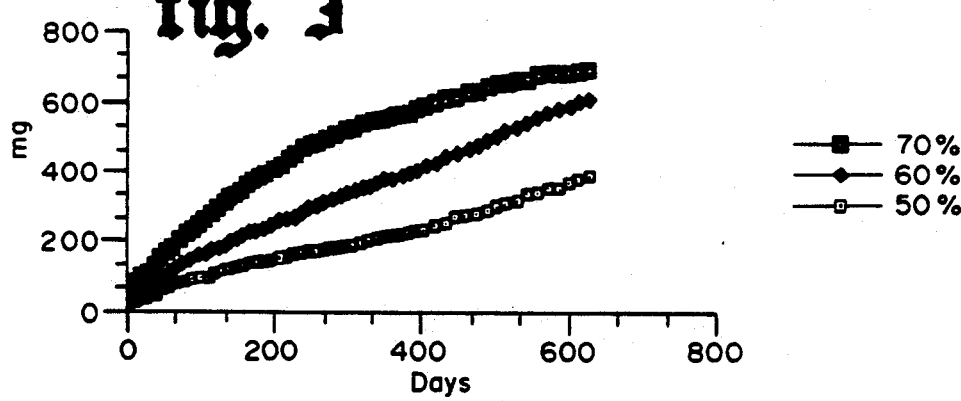
FIG. 3 is a graph showing the cumulative L-DOPA release from polymers which were surrounded by a non-permeable coat on all but one side of the slab.
Figure 4:
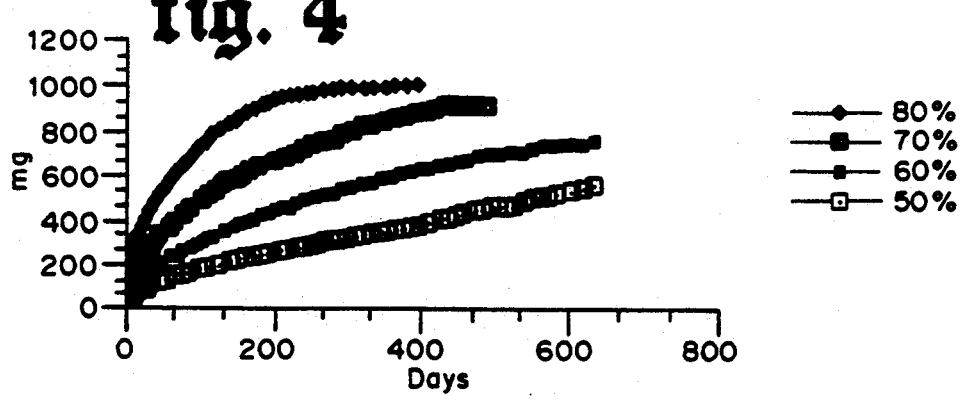
FIG. 4 is a graph showing the cumulative L-DOPA release from polymers which were not surrounded by a coat, showing linear release of L-DOPA.

The results are shown in FIGS. 2-4, indicating that controlled-release of L-DOPA was achieved for long time periods under all conditions. FIG. 2 is a graph showing the cumulative L-DOPA release from polymers which were surrounded by a non-permeable coat containing a 2 mm hole. FIG. 3 is a graph showing the cumulative L-DOPA release from polymers which were surrounded by a non-permeable coat on all but one side of the slab. FIG. 4 is a graph showing the cumulative L-DOPA release from polymers which were not surrounded by a coat, showing linear release of L-DOPA.

To assess whether the "impermeable" coat does indeed prevent the diffusion of L-DOPA, the potential release of polymer samples which were fully coated was measured. With the exception of one defective sample, in the 125-day period studied, these controls did not release L-DOPA. The measurement of blank control polymers without coat also did not result in absorbance and confirms that the absorbance values are not an artifact of polymer breakdown products.

The effects of L-DOPA loading on release kinetics were studied by comparing polymers with different loading, ranging from 50%–75%, which were surrounded by an impenetrable barrier as described by the prior art, Rhine et al., ibid, leaving open a pore of 2 mm diameter (FIG. 2). Controlled-release was obtained in all cases and the quantity released correlated with loading.

In order to increase the absolute amount of release, the release pattern of L-DOPA from polymers, which had an entire side of the slab exposed to the solution and all other sides surrounded by an impermeable coating, was examined. Zero-order kinetics was achieved in all polymers, irrespective of their loading (50, 60 or 70%). The polymers released L-DOPA in the mg-range per day and release continued beyond 500 days. Note that the linear range is shorter in polymers with high loading, suggesting that the polymer is emptying out after about 300 days. In contrast, release remains linear in 50 and 60% loading samples for an extended period of time (FIG. 3). Even non-coated polymers display linear release. As FIG. 4 shows, the 50 and 60% loaded polymers release linearly for at least 600 days, and some linearity is even found in the 70% samples.

Some polymeric devices with only 30% loading have also been tested, but no appreciable release was found. This finding suggests that the proposed mechanism of release (diffusion through communicating channels and pores) is applicable to these devices and that loading of EVA devices at 30% concentration of L-DOPA apparently did not permit sufficient development of pores and communicating channels. The higher the loading of the polymer with drug particles, the more pores and communicating channels are formed, resulting in greatly increased absolute quantities of release, which cannot be explained simply by the greater total quantity of drug in the polymer. Thus low molecular weight water soluble substances are released from polymers with high loading by a mechanism which is substantially different from that reported by the prior art for such molecules, allowing the releasable quantity of water-soluble drug to be greatly enhanced.

FIG. 5 demonstrates the cumulative in vitro release of dopamine from a variety of polymer configurations. This cumulative release was directly proportional to the square root of time, suggesting that diffusion of the encapsulated solute from the polymer was the rate limiting step in the release process. Since release of dopamine from the device was totally eliminated by coating with a thin layer of EVAc, the EVAc must be impermeable to the dopamine. Therefore, release of dopamine from the polymer must occur through a network of interconnected, aqueous pores, as shown in FIG. 6. FIG. 6 is a schematic cross-section of the dopamine/copolymer devices of FIG. 5 showing the solid particles (dark) of dopamine encapsulated in a continuous polymer phase. Although the polymer phase is impermeable to the encapsulated molecules, release occurs as water enters the pore space, dissolving the solid particles. Molecules counter diffuse of the polymer through the pore network created by dissolution.

Assuming that dopamine solubility in aqueous buffer ($C_s$) is high, the diameter of the internal pores is less than the thickness of the device, and release occurs predominantly in one dimension through the two largest faces of the slab, the release process can be described by the continuum diffusion equation:

$$\frac{\partial C}{\partial t} = D_{eff} \frac{\partial^2 C}{\partial x^2} \quad [1]$$

where x is the position, t is time following immersion in buffer, C is the concentration of dopamine in the matrix at position x and time t, and $D_{eff}$ is the effective diffusion coefficient of dopamine through the pore space. Appropriate boundary and initial conditions for this formulations are:

$$C = C_o \quad \text{at } t = 0 \quad \text{for } 0 < x < L \quad [2]$$
$$C = 0 \quad \text{at } x = 0, L \quad \text{for } t > 0$$

The complete solution to this equation, yielding C as a function of x and t, for the stated boundary conditions is described by Crank, *The Mathematics of Diffusion* 2nd edition (Oxford Press, London, 1972). The mass of solute released at any time is found by integrating the expression for C to find the mass of solute remaining in the slab. For short times, when more than 40% of the encapsulated solute remains in the slab, the mass of solute released, $M_t$, is proportional to the square root of time:

$$M_t = 4M_o \sqrt{\frac{D'_{eff}}{L^2 \pi}} \quad [3]$$

where $M_o$ is the mass of solute initially present in the matrix.

Figure 5A:
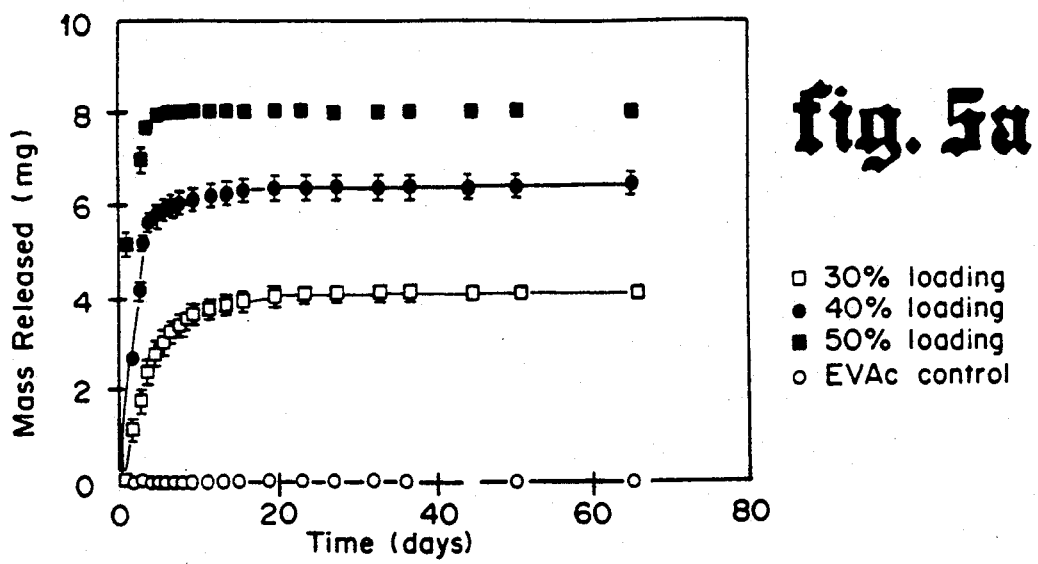
FIGS. 5a, 5b, 5c are the release of dopamine from dopamine/ethylene vinyl acetate copolymer matrices. Each experimental point represents the mean (± standard deviation) cumulative mass of dopamine released for 4 sample matrices. Each dopamine/polymer matrix initially contained 0% (empty circle), 30% (empty square), 40% (filled circle), or 50% (filled square by weight dopamine. The cumulative mass of dopamine released is shown by matrices with different geometries: a) a simple disc, b) a disc with one impermeable face, and c) a disc with a completely impermeable coating except for a single cavity in one face. Solid lines in the bottom panel demonstrate the linear release predicted by a model of diffusion of dopamine through the prescribed geometry. The cumulative mass of dopamine released is shown for matrices with different geometries: 5a) a simple disc, 5b) a disc with one impermeable face, and 5c) a disc with a completely impermeable coating except for a single cavity in one face. Solid lines in the bottom panel demonstrate the linear release predicted by a model of diffusion of dopamine through the prescribed geometry.

Comparison of the release profiles shown in FIG. 5a with equation 3 yields an experimental value for the effective diffusion coefficient. The experimentally determined effective diffusion coefficients for dopamine in the polymer pore space depend on the mass of dopamine initially incorporated within the matrix, as shown in Table 1. This is consistent with previously observed results for release of other bioactive agents from EVAc slabs.

Figure 5B:
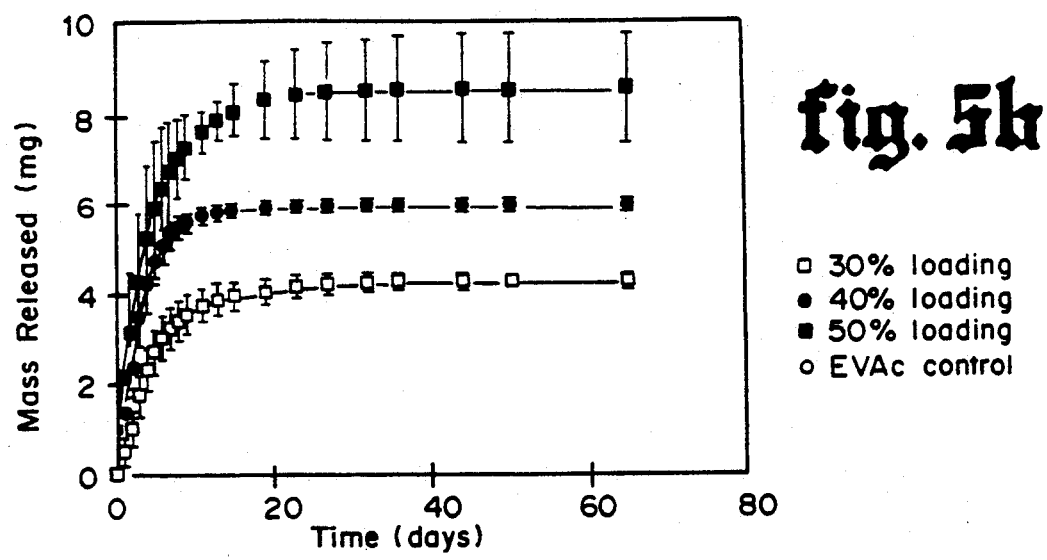

Although the absolute value of mass released changed, the same dependence of release on the square root of time was observed when the devices were coated with an impermeable polymer layer on one face (FIG. 5b). This is the expected behavior for release from a slab with one impermeable boundary.

Figure 5C:
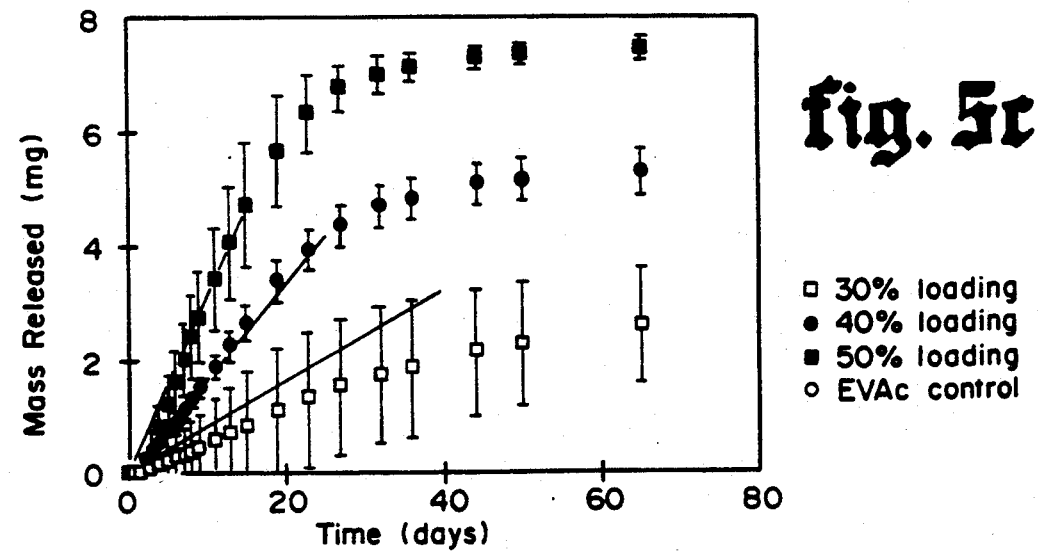

With a complete EVAc coating over the matrix, no solute was released over the 65 day period. When a single cavity was introduced into the impermeable coating, release was linear with time (FIG. 5c). Release rate of 0.06, 0.17, and 0.30 mg/day were obtained from matrices of 30, 40, and 50% loading, respectively. For times when less than approximately 60% of the initially encapsulated solute has been released, this configuration should behave as a coated hemispherical vehicle. As described by Rhine, et al., (1980), this geometry produces zero order (linear) release kinetics and the rate of release is related to physical properties of the solute and the polymer phase by:

$$M_t = 2\pi C_s D_{eff} R t \quad [4]$$

where R is the radius of the exit cavity in the impermeable polymer phase.

Using the effective diffusion coefficients, and assuming $C_s R = 60$ mg/cm$^2$, a constant for all matrices, the predictions of this model are compared with the experimental data in FIG. 5c. The effective diffusion coefficient was determined from independent experiments in the geometrically simple matrix. This model agrees well with the experimental data.

Observed release from the fully coated matrix except for a single exit cavity suggests that a constant rate of dopamine release can be provided by this simple matrix device for at least a 15-50 day period. Service life of the matrix depends on the initial concentration of solute in the matrix and the absolute size of the device. Equation 4 is valid during the time when the coated device behaves as a coated hemisphere. For a given solute, this can be increased by increasing the physical dimensions (i.e. diameter and depth) of the matrix.

Release was also monitored from several linear release matrix devices over a several hour time period to insure that release does not fluctuate over a time course shorter than one day. As demonstrated in FIG. 7, the release of dopamine was constant over the short term, as well.

This study demonstrates that long-term, controlled release of dopamine can be achieved in vitro by using recently developed controlled release technology. When dopamine copolymer matrices (30% loading, in the presence of a full coating and a single cavity) were implanted adjacent to the corpus striatum in rats, striatal extracellular fluid concentrations of dopamine as measured by intracerebral dialysis were found to be elevated up to 7 $\mu$M, over 200-fold greater than control values.

Although the studies were performed using ethylene-vinyl acetate as a biocompatible copolymer, biodegradable polymers such as polyanhydrides, could also be used. Furthermore, microspheres (miniature spherical copolymer devices, 10-500 $\mu$m in diameter) containing polymer/dopamine (or other substances) could be utilized which could be injected into discrete brain regions through a syringe, obviating the need for complicated surgery. In addition, by embedding small magnets within the device which modulate the access of the imbedded substance to the extracellular fluid, an appropriate external electromagnetic field can control the release rate.

Variations of this technology allow controlled, sustained release of almost any biologically active substance, including dopamine, effective in the treatment of a variety of disorders, as well as proteins, including disorders of the nervous system such as those involving missing lysosomal enzymes or defective enzymes in such storage diseases as Tay Sachs Disease.

Modifications and variations of the present invention, polymeric compositions for extended delivery of small molecular weight, water-soluble molecules, will be obvious to those skilled in the art from the foregoing detailed description of the invention. Such modifications and variations are intended to come within the scope of the appended claims.

We claim:

1. A polymeric composition for extended term delivery of low molecular weight, less than or equal to 1,000 water-soluble molecules following implantation in a patient comprising
   biologically active, low molecular weight, water-soluble molecules to be delivered, the molecules being selected from the group of biologically active molecules consisting of proteins, carbohydrates, inorganic molecules, organic molecules, nucleic acids, and minerals, and
   a matrix, consisting essentially of a polymer selected from the group consisting of acyl substituted cellulose acetates and alkyl derivatives thereof; partially and completely hydrolyzed alkylene-vinyl acetate copolymers, unplasticized polyvinyl chloride, crosslinked homo- and copolymers of polyvinyl acetate, crosslinked polyesters of acrylic and methacrylate; polyvinyl alkyl ethers; polyvinyl fluoride, silicone; polycarbonate, polyurethane; polyamide, polysulphones; styrene acrylonitrile copolymers, crosslinked poly(ethylene oxide); poly(alkylenes); poly(vinyl imidazole); poly(esters); poly(ethylene terephthalate); and chlorosulphonated polyolefines wherein the polymer is biocompatible and resistant to chemical and physical destruction at the site of implantation,
   the biologically active molecules being dispersed within the polymer matrix in a concentration within a sufficient number of pores and channels to the exterior of the matrix to result in linear diffusion of the dispersed molecules out of the matrix over an extended time period at a release rate controlled by the loading of the polymer matrix with the biologically active molecules.

2. The polymeric composition of claim 1 wherein the polymeric matrix is covered in part with an impermeable coating, said coating leaving sufficient exposed pores and channels to allow linear diffusion of the dispersed molecules out of the matrix over an extended period of time.

3. A method for extended term delivery of low molecular weight, less than or equal to 1,000 water-soluble molecules following implantation in a patient comprising
   providing biologically active, low molecular weight, water-soluble molecules to be delivered, the molecules being selected from the group of biologically active molecules consisting of proteins, carbohydrates, inorganic molecules, organic molecules, nucleic acids, and minerals and
   a matrix, consisting essentially of a polymer selected from the group consisting of acyl substituted cellulose acetates and alkyl derivatives thereof; partially and completely hydrolyzed alkylene-vinyl acetate copolymers, unplasticized polyvinyl chloride, crosslinked homo- and copolymers of polyvinyl acetate, crosslinked polyesters of acrylic and methacrylate; polyvinyl alkyl ethers; polyvinyl fluoride, silicone; polycarbonate, polyurethane; polyamide, polysulphones; styrene acrylonitrile copolymers, crosslinked poly(ethylene oxide); poly(alkylenes); poly(vinyl imidazole); poly(esters); poly(ethylene terephthalate); and chlorosulphonated polyolefines wherein the polymer is biocompatible and resistant to chemical and physical destruction at the site of implantation,
   the biologically active molecules being dispersed within the polymer matrix in a concentration within a sufficient number of pores and channels to the exterior of the matrix to result in linear diffusion of the dispersed molecules out of the matrix over an extended time period at a release rate controlled by the loading of the polymer matrix with the biologically active molecules.

4. The method of claim 3 further comprising covering in part the polymeric matrix with an impermeable coating, said coating leaving sufficient exposed pores and channels to allow linear diffusion of the dispersed molecules out of the matrix over an extended period of time.

5. The method of claim 3 further comprising implanting the polymeric composition.

* * * * *